US005637104A

United States Patent [19]
Ball et al.

[11] Patent Number: 5,637,104
[45] Date of Patent: Jun. 10, 1997

[54] LOCKING CAP FOR THE POUR SPOUT OF A SUCTION CONTAINER

[75] Inventors: Art E. Ball; Stephen M. Burgess; John C. Dargis; Martin V. Maier, all of Salt Lake City; Matthew D. Wold, So. Ogden, all of Utah

[73] Assignee: Abbott Laboratories, Abbott Park, Ill.

[21] Appl. No.: 490,960

[22] Filed: Jun. 15, 1995

[51] Int. Cl.[6] .................... A61M 1/00; B65D 41/06
[52] U.S. Cl. .................... 604/319; 604/317; 604/905; 220/296; 220/300
[58] Field of Search ...................... 604/317–326, 604/403, 905; 220/254, 293, 298, 300–302, 375, 215, 222, 296; 215/200

[56] References Cited

U.S. PATENT DOCUMENTS

| | | | |
|---|---|---|---|
| 2,044,276 | 6/1936 | Bukolt | 220/298 |
| 3,048,317 | 8/1962 | Cochrane et al. | 220/254 |
| 4,133,560 | 1/1979 | Ishikawa et al. | 220/293 |
| 4,321,922 | 3/1982 | Deaton | 604/319 |
| 4,347,946 | 9/1982 | Nichols | 604/319 |
| 4,460,361 | 7/1984 | Nichols | 604/319 |
| 4,485,075 | 11/1984 | Stotz et al. | 220/301 |
| 4,487,606 | 12/1984 | Leviton et al. | 604/319 |
| 5,329,971 | 7/1994 | Condon | 220/293 |
| 5,443,175 | 8/1995 | Kelly et al. | 220/375 |
| 5,529,201 | 6/1996 | Talbert | 220/302 |

*Primary Examiner*—John G. Weiss
*Assistant Examiner*—David J. Cho
*Attorney, Agent, or Firm*—Brian R. Woodworth

[57] ABSTRACT

A suction container usable to suction fluids from the surgical field in an operating room environment. The container has a rigid cover overlying a flexible body portion attached thereto, the cover including a pour spout having a tubular body portion, a segmented thread disposed on an inner wall as a tubular body, the thread having a plurality of spaced segments, each segment defining a ramp and a stop. A locking cap is provided for mounting on the pour spout, the locking cap having a complementary tubular body for insertion into the pour spout, with complementary spaced ramped locking elements disposed on an outer surface of the tubular body for engaging the thread segments in locking the cap on the pour spout in fluid-tight engagement.

13 Claims, 4 Drawing Sheets

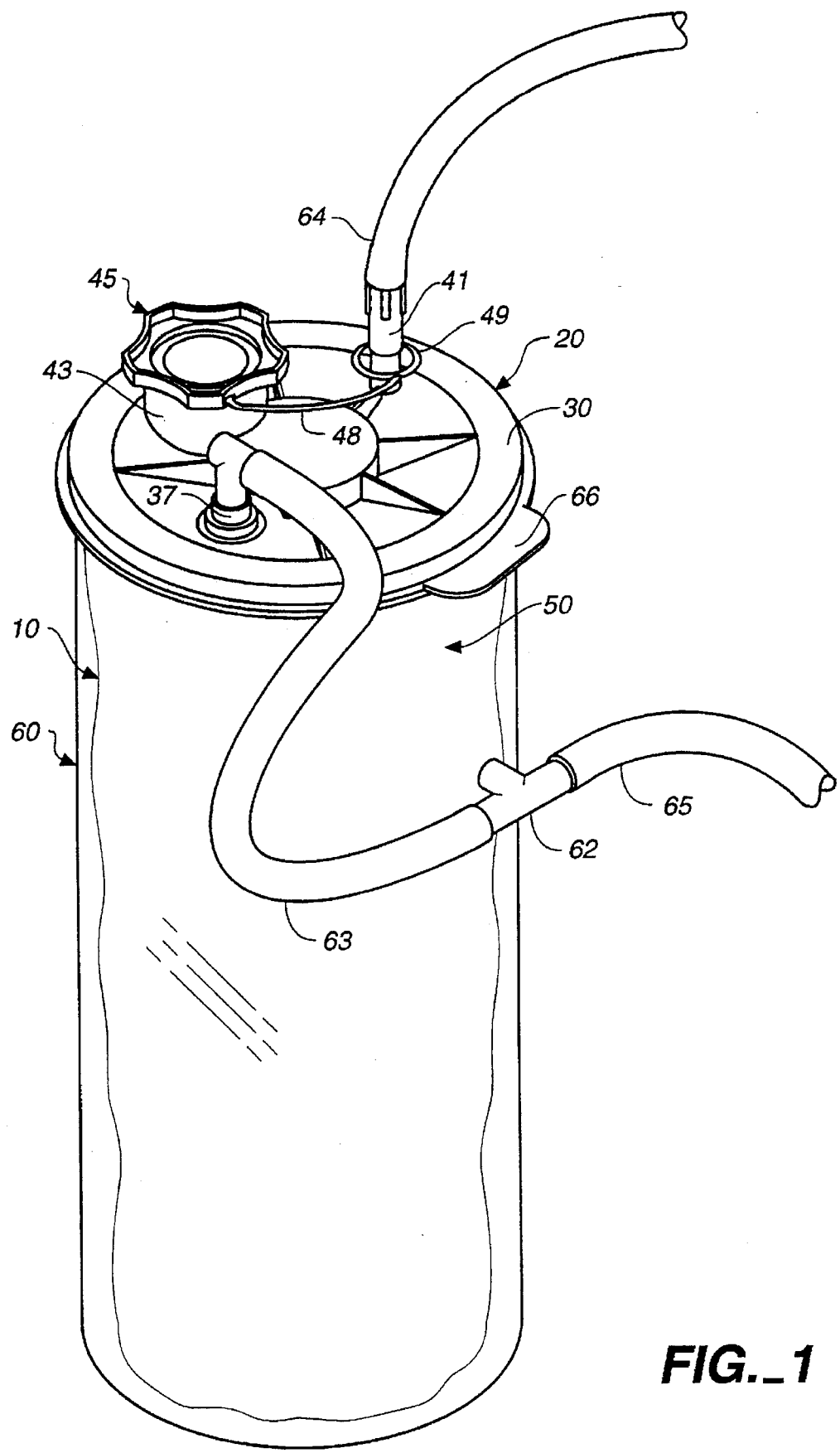
FIG._1

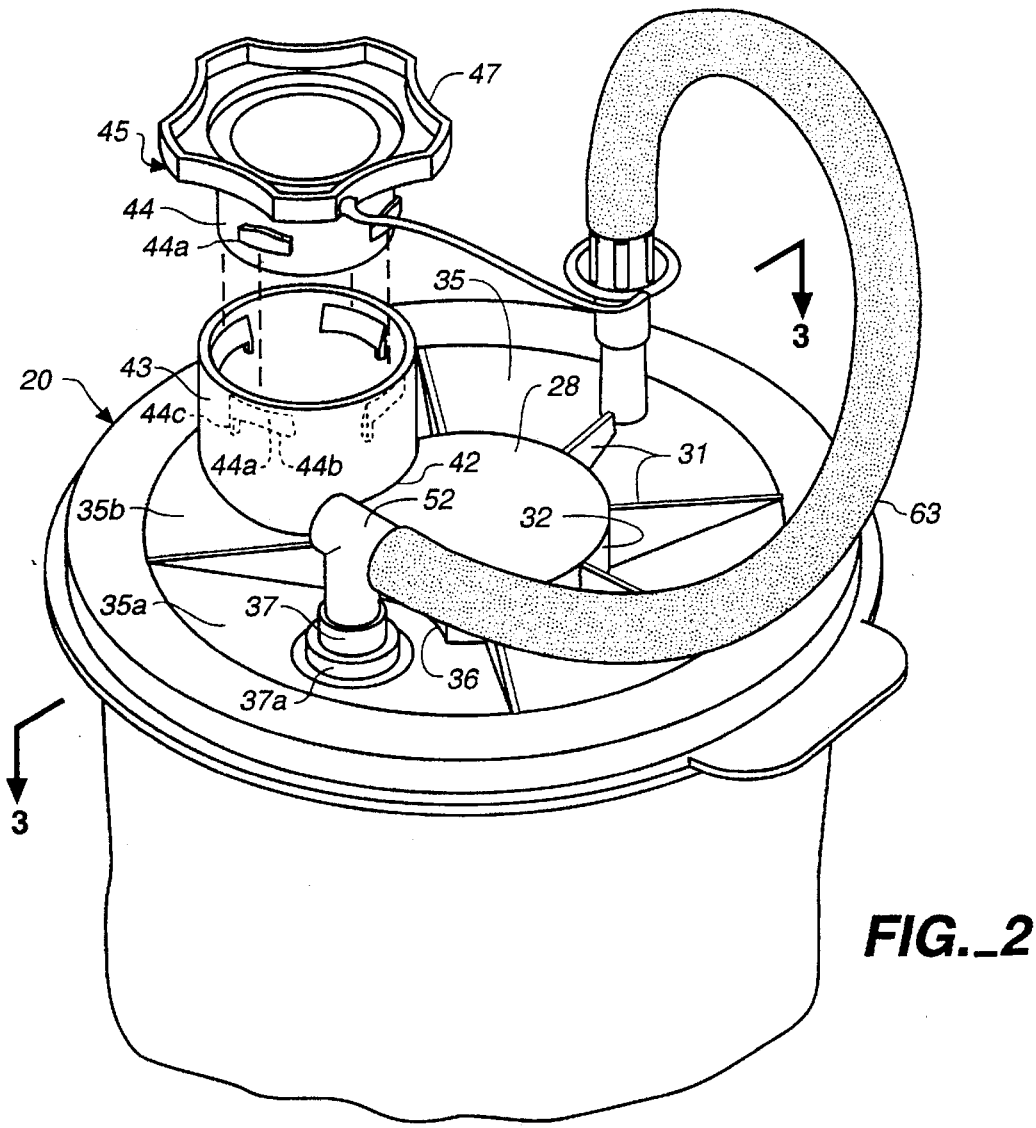
FIG._2
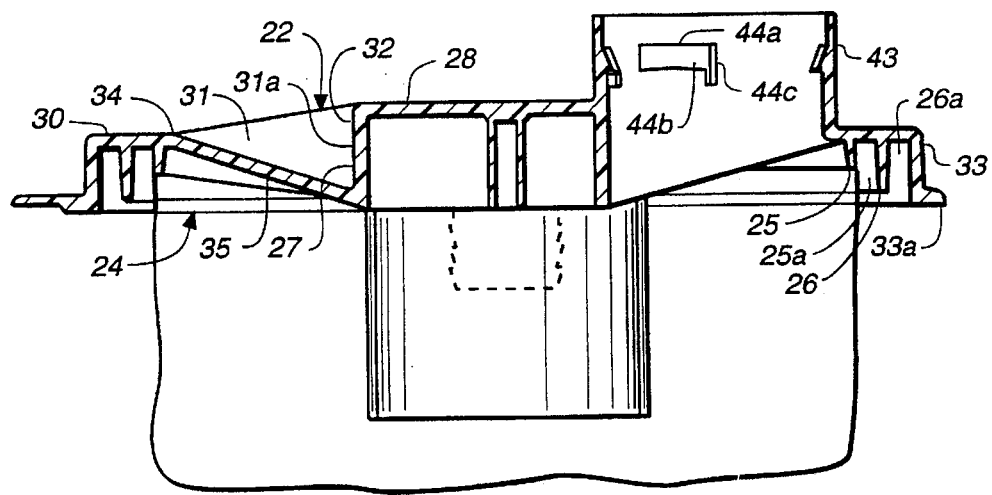
FIG._5

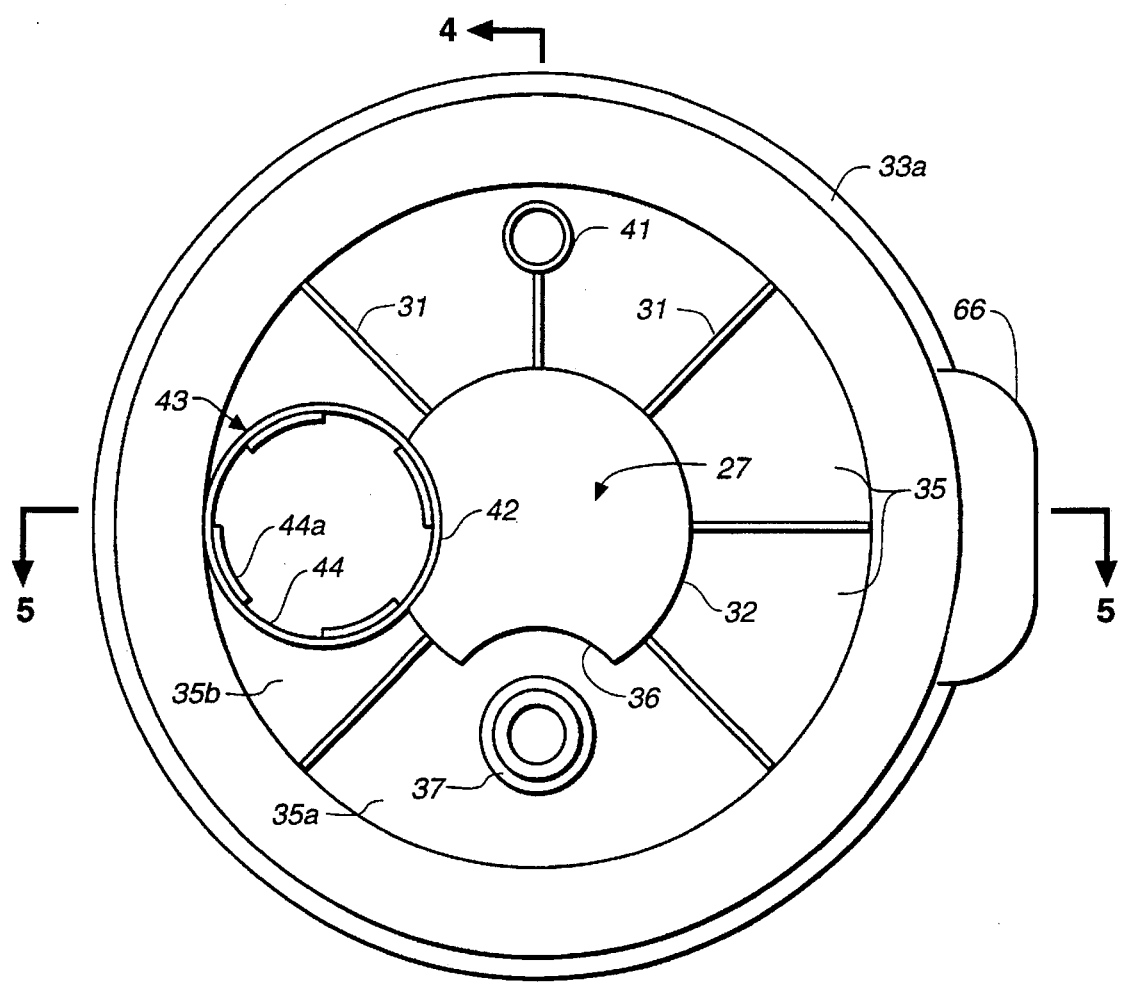
FIG._3
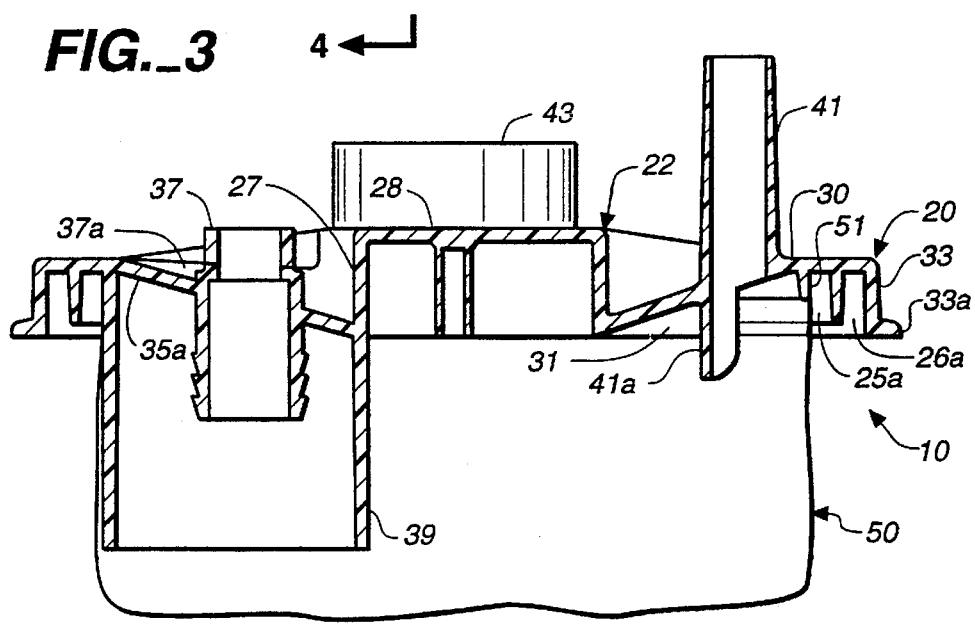
FIG._4

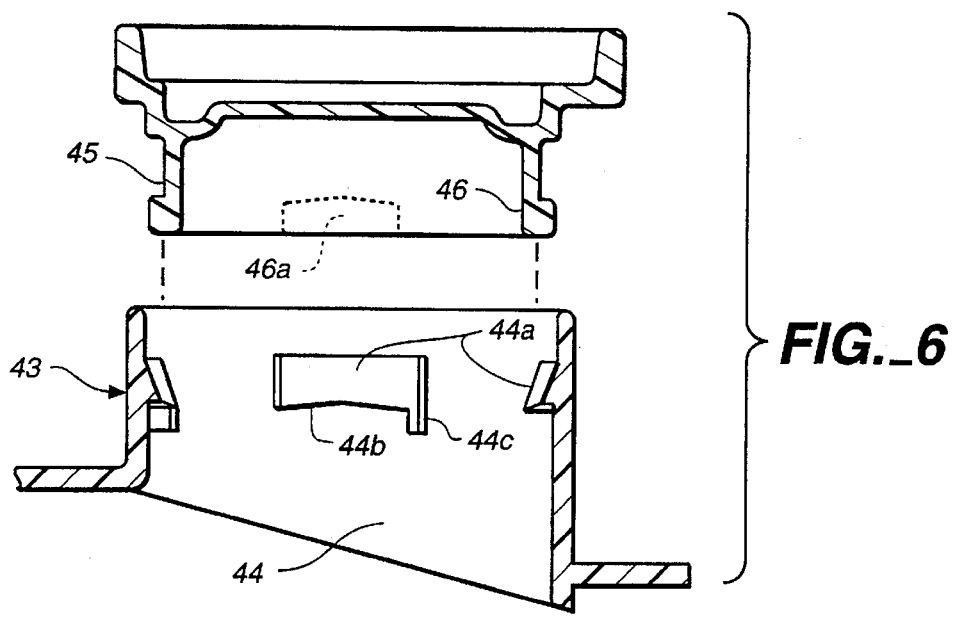
*FIG._6*
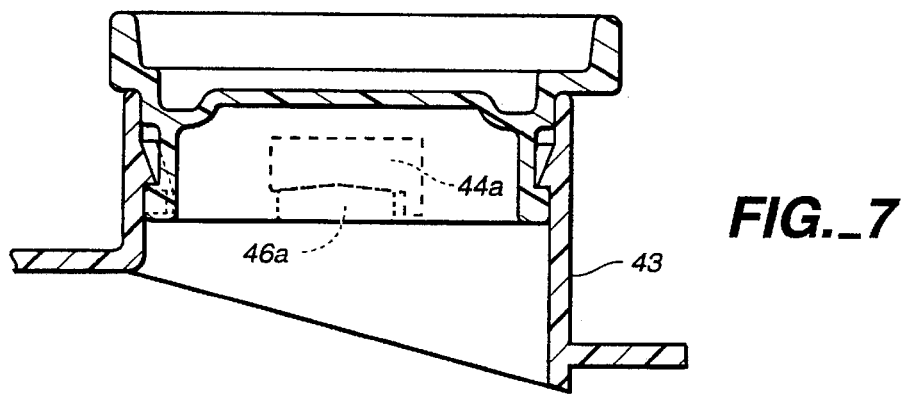
*FIG._7*
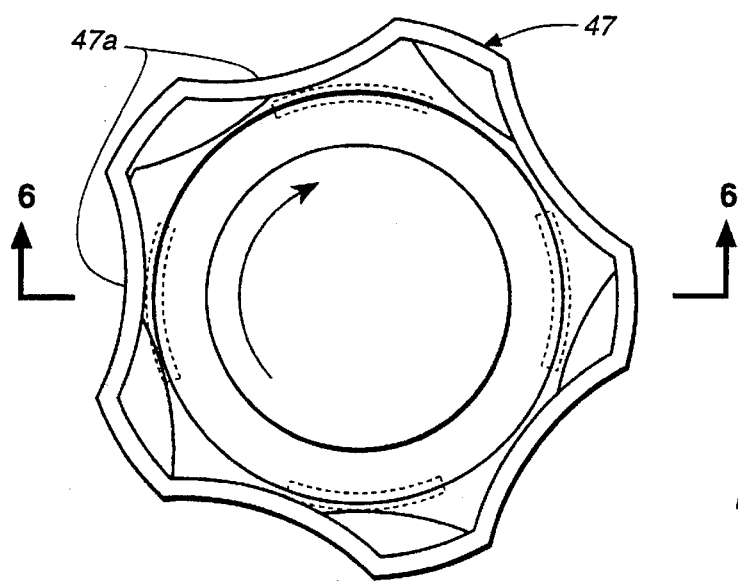
*FIG._8*

LOCKING CAP FOR THE POUR SPOUT OF A SUCTION CONTAINER

FIELD OF THE INVENTION

The invention generally relates to fluid suction containers and in particular, to locking caps used with the pour spout of such containers.

BACKGROUND OF THE INVENTION

Typically a fluid suction container is used in a medical application such as an operating room environment to draw excess fluids away from a surgical field whether such fluids are medical fluids used to irrigate the surgical fluid or the patient's own excess body fluids.

One form of the suction container is a hard plastic canister having a removable cover thereon, with an air-tight seal between the cover and the canister so as to allow a vacuum to be operable within the canister to facilitate the withdrawal of excess fluids from the surgical field.

Because the canister is rigid and must be of sufficient strength to withstand the vacuum forces operative within the canister during its period of use, the cover is a point of weakness for the canister and must be designed to have sufficient strength and rigidity to prevent it from being drawn into the canister under the vacuum forces in use. Moreover, it is desirable that the cover have means therein to dispose of the fluid collected in the canister during its use in the medical procedure involved.

Because use of a rigid canister required the disposal of medical fluids collected therein, and sterilization after each usage, an alternative configuration for a suction container was proposed. In such alternative configuration a flexible canister liner was attached to a cover to be mounted on a rigid canister with such cover still maintaining sealing means with respect to the canister to assure the integrity of the vacuum provided in the rigid canister. In the alternative container configuration employing a hard cover attached to a flexible liner, such vacuum means is first used to draw the flexible container to its full volume before initiating fluid suction. The vacuum then applies suction to draw excess fluids from the surgical field into the flexible liner during the medical procedure involved, and then the cover and attached liner are removed from the rigid canister for disposal. And, such suction container comprising a rigid cover and a flexible liner can be disposed of after a single usage.

However, whether a suction container cover only is mounted on a rigid canister or the suction cover and its attached flexible liner is mounted on the rigid canister, it may be necessary to dispose of medical fluids after the medical procedure is performed through a pour spout in the cover. In both instances, the pour spout must be positively closed during the medical procedure to enable a vacuum condition for suction within the container and then capable of being opened for pouring of collected fluids from the container for disposal. With PVC cover materials it was possible to use a threaded cap and pour spout to secure the cap on the pour spout in fluid-tight and air-tight engagement. However, for many hospitals it is desirable to use something other than PVC materials for disposable containers, and typically such other materials are incapable of providing a threaded fluid-tight, air-tight connection.

In some instances, it is not necessary to reopen a suction container for disposal of fluids held therein, since many hospitals will incinerate waste containers, fluids and all. However, a substantial number of hospitals prefer to dispose of waste fluids and suction containers separately.

SUMMARY OF THE INVENTION

Accordingly, it would be desirable to provide a pour spout and cap combination which is usable with a preferred manufacturing material for suction containers such as polyethylene. The spout and cap combination are capable of being securely locked in fluid-tight, air-tight engagement for use in waste fluid suction procedures and then capable of being opened to separately dispose of the containers and the waste fluids in the containers.

Accordingly, the present invention provides a cover of sufficient strength to be mounted on a rigid canister, the cover receiving at an inner end a flexible canister liner for waste fluids attached to the cover in air-tight engagement, such cover including a pour spout and cap combination lockable in fluid-tight, air-tight engagement.

The pour spout should include a tubular body, opened at both ends and having at an inner surface thereof a segmented thread, each segment including a ramp and a stop, the segments equally spaced at 90 degree intervals. The complementary engaging cap should have a tubular body which snugly fits into the tubular body of the pour spout with equi-spaced ramps complementary to the locking segments of the pour spout for firmly locking the cap in place on the pour spout. Additional features of the cap would include support vanes or ribs to add structural integrity to the cap, and an oversized gripping surface indented to provide gripping segments for manual or automated gripping to rotate the cap into locking engagement on the pour spout.

A better understanding of the present invention can be obtained by considering the drawings briefly described below with the detailed description of the preferred embodiment which follows.

BRIEF DESCRIPTION OF THE DRAWINGS

FIG. 1 is a perspective view of a flexible container mounted on a rigid shell also showing a first tubing section connecting the flexible container to a vacuum source and a second tubing section connecting the container to a patient;

FIG. 2 is an exploded perspective view showing the flexible container including a portion of the liner as well as a closing cap associated with the pour spout and separated therefrom;

FIG. 3 is a bottom plan view taken along the lines 3—3 of FIG. 3;

FIG. 4 is a sectional view taken along the lines 4—4 of FIG. 3;

FIG. 5 is a sectional view taken along the lines 5—5 of FIG. 3;

FIG. 6 is an exploded sectional elevation taken along the lines 6—6 of FIG. 8 in which the pour spout and the locking cap are separated;

FIG. 7 is a view similar to FIG. 6 in which the locking cap is mounted in place on the pour spout; and FIG. 8 is a top plan view of the locking cap mounted and closed onto the pour spout.

DETAILED DESCRIPTION OF THE PREFERRED EMBODIMENT

In FIGS. 1 and 2 is shown the flexible container 10 used as a receptacle for waste fluid in the operating room. The flexible container 10 comprises a cover 20 and flexible liner 50 received in a rigid shell or canister 60. The liner 50 and rigid canister 60 are discussed in greater detail below.

The cover 20, better seen in FIGS. 3–5, is a one piece molded construction of relatively rigid material such as polyethylene. Typically, polyethylene and similar plastics are not good choices for threaded parts because slippage occurs between joined parts, and it is difficult to achieve an air-tight, fluid-tight connection when polyethylene threaded parts are joined. The cover 20 includes an upper face 22 and lower face 24.

Shown on the lower face 24 (FIGS. 4 and 5) are a pair of annular flanges 25 and 26 which will be described in more detail below. The upper face 22 of the cover 20 includes a central support cylinder 27 closed at its upper face as at 28. The support cylinder 27 is concentric with the center of cover 20 and is 1.50 inches in diameter, slightly larger than one-third the diameter of the cover, which is 4.38 inches in diameter.

The upper face 22 of the cover 20 also includes an outer ring 30 displaced from central cylinder 27. The ring 30 overlies the inner annular flange 25 and outer annular flange 26 on the lower face 24 of the cover. The upper face of the ring 30 is disposed slightly below the upper face 28 of the central cylinder 27. At an outer edge of ring 30 is a downwardly extending outer annular wall 33. Outer annular wall 33 is also disposed adjacent outer flange 26. An annular bead 33a is also provided at the lower edge of the outer wall 33 to provide increased structural integrity under vacuum conditions.

Extending radially from the center of cover 20 to the inner edge of the first lower annular flange 25 are a plurality of equi-spaced ribs or vanes 31. At an edge 32 where the vanes 31 extend through the central cylinder 27, the vanes are the same height as the central cylinder. However, the vanes 31 are triangular in shape, with a base 31a (FIG. 5) engaging the central cylinder 27, and tapering in width as each vane extends from its base engaging the central cylinder to the inner edge of the outer ring 30 of the cover 20 to terminate at a point 34 (FIG. 5) at an inner edge of the ring 30.

Disposed between adjacent vanes 31 are cover segments 35 which begin at the inner edge of outer ring 30 and project inwardly and downwardly to engage the central cylinder 27 at a lower edge thereof.

The central cylinder 27 is also truncated at two sections. At section 36, the first of these truncated sections, a vacuum port 37 is disposed on a widened segment 35a, about midway between the rim 30 and the truncated portion 36. Vacuum port 37 protrudes above the widened segment 35a which has no vane 31 on its upper surface.

The vacuum port 37 extends above the cover 20 to about the height of the central cylinder 27. Port 37 includes a shoulder 37a disposed in the upper plane of segment 35a. On the lower face 24 of the cover 20 opposite the vacuum port 37 is a cylinder or skirt 39 (FIG. 4) which will be described in more detail below. Opposite the vacuum port 37 on the upper face 22 of the cover 20 is a tubular patient port 41, which intersects a vane 31 between adjacent segments 35 and is about 0.30 inches in diameter and extends about 1.00 inches above the outer ring 30 of the cover.

About midway between the vacuum port 37 and the patient port 41 is a second truncation 42 of the central cylinder 27. A widened segment 35b receives a pour spout 43 which is slightly larger than 1.00 inches in diameter and extends above the upper face 22 of the cover 20 about 0.60 inches.

At the lower face 24 of the cover 20, vanes 31 protrude slightly below lower face 24 and terminate at inner flange 25. Flanges 25 and 26, and flange 26 and outer wall 33, respectively, define annular spaces 25a and 26a therebetween. Inner annular space 25a receives the flexible liner 50 which is disposed against an outer face 51 of flange 25 and is fastened against face 51 of flange 25 in fluid-tight, air-tight engagement, as by welding. Annular space 26a, between outer flange 26 and outer wall 33 is provided for a purpose described in detail below.

The cylindrical skirt 39 of vacuum port 37 is slightly larger than 1.00 inches in diameter and is slightly longer than 1.00 inches. An upper extension of skirt 39 truncates central cylinder 27 at section 36. Skirt 39 holds a non-mechanical valve therein which will not be described in detail since it is not the subject of the present invention. The skirt 39 also includes a plurality of spaced structural vertical vanes (not shown) extending downwardly from the lower face 24 of cover 20.

The patient port 41 at its lower end includes a semi-circular splash guard 41a whose outer edge faces the vacuum port 37 and extends about 0.50 inches below the lower face 24 of the cover 20.

The tubular pour spout 43 terminates at the lower face 24 of the cover 20 and its lower edge slopes upwardly continuously with the segment 35b. The pour spout 43 is shown in more detail with its overlying cap 45 in FIGS. 6 through 8.

The tubular pour spout 43 includes a series of locking segments 44a equi-spaced on an inner face 44 of the pour spout 43. There are four locking segments 44a on inner face 44 of the pour spout 43, and they are disposed 90 degrees apart.

Each locking segment 44a includes a ramp 44b and a stop 44c at inner face 44 thereof. Complementary locking elements 46a are disposed on the outer periphery of a tubular body portion 46 of the cap 45. The tubular body portion 46 of the cap 45 fits into the tubular pour spout 43 to assure an air-tight, fluid-tight interface when the locking cap is locked in place on the pour spout. Each locking element 46a is ramp-shaped and in complementary conformance to the ramp 43b of each thread segment.

An outer gripping portion 47 of the cap 45 is fluted to provide multiple grip areas 47a at the outer edge of the cap 45 to enable manual or automated gripping. It would be desirable to use an automated gripping mechanism to engage locking cap 45 on pour spout 43 for closing during manufacture. Cap 45 can also be attached to the cover 20 by a link. A holding ring 49 at the end of link 48 may be attached to the cover 20 as at patient port 41. Actually, it is preferable that the link or holding ring 49 be mounted on elbow 52 inserted in the vacuum port 41, to better retain the link on the cover since the elbow 52 is not removed from the cover once vacuum tubing 63 is in place. However, to better display all of the structural elements of the invention, the link 49 was attached to patient port 41 in FIGS. 1–2.

The cover 20 is installed onto a waste canister 60 as follows. The waste canister 60 (FIG. 1) is a rigid canister body formed of a clear plastic such as a polycarbonate. It is also useful for the waste canister 60 to have volume markings on it to show the amount of fluid collected. Typically, those markings are in milliliters, and thus, satisfies both U.S. and foreign needs.

The flexible suction container 10, comprising the cover 20 and the flexible liner 50, is extended to its full length and fully inserted into the canister 60. The cover 20 is then snapped onto the canister 60, trapping the upper cylindrical edge of the canister 60 in space 26a between cover outer wall 33 and annular flange 26 to mount the cover 20 on the canister in air-tight engagement.

With the cover 20 firmly in place, the canister vacuum source is connected by tubing 65 to the right side of a tee fitting 62. The vacuum source is then activated to cause the flexible liner 50 to be drawn tightly against the inner face of the canister 60. Then the lid liner tubing 63 is attached to the left side of the tee at one end and to elbow 52 at an opposite end. Elbow 52 is then inserted into the vacuum port 37. A proximal end of patient tubing 64 is attached to the patient port 41 for fluid suction. The vacuum generated during fluid suction is typically 20 inches of mercury, but the suction container is operable at a vacuum of 10 inches of mercury.

The process of removing the liner from the canister begins with the vacuum turned on. First, the lid liner tubing 63 is detached from the canister tee fitting 62 with a downward twisting motion. Then the patient tubing 64 is detached from patient port 41. Then the lid liner tubing 63 is re-attached to patient port 41. Then the vacuum is turned off. Then, using thumb pressure on a tab 66 provided at a lower edge of cover 20, the cover 20 is loosened from the canister 60 and removed.

Following removal of the suction container 10 from the canister 60, the collected waste fluids can be disposed of by unlocking the cap 45 from the pour spout 43 to dispose of the waste fluid separately from the suction container, or the suction container and waste fluids may be disposed of together by leaving the system intact.

While the present invention has been disclosed with respect to the preferred embodiment, those of ordinary skill in the art will understand that further modifications may be made within the scope of the claims that follow. Accordingly, it is not intended that the claims be limited by the disclosure of the preferred embodiment, but that the scope of the invention be determined solely by reference to the claims.

The embodiment of the invention in which an exclusive property or privileges is claimed is defined as follows:

We claim:

1. In a suction container useable to suction fluids from the surgical field of a patient in an operating room environment, a rigid cover overlying a flexible body portion of the container and attached thereto, the cover comprising:

a circular engagement member including an upper face, a lower face, an annular outer rim, and a plurality of downwardly directed annular flanges successively displaced inwardly from said outer rim, at least one of said flanges being attached to the flexible body portion;

a plurality of spaced-apart support vanes extending generally from the center of the cover to the periphery thereof to divide the cover into a plurality of segments disposed between the support vanes;

a support cylinder concentrically disposed about the center of the cover, closed at an upper face thereof, and intersecting the support vanes, said segments disposed between the support vanes extending from the annular outer rim to a base of the support cylinder;

a plurality of openings in the cover, including a patient port, a vacuum port and a pour spout, said pour spout including a tubular body portion;

a locking cap for the pour spout, said locking cap having a complementary tubular body for insertion into the tubular body portion of the pour spout;

means for coupling the locking cap into sealing engagement with the pour spout, said means comprising a segmented thread having a plurality of segments, each segment defining a ramp and a stop, and a plurality of complementary ramped locking elements, one of the segments and the ramped locking elements being disposed at spaced-apart intervals around an inner wall of the tubular body portion of the pour spout, and the other of the segments and the ramped locking elements being disposed at spaced-apart intervals around an outer surface of the tubular body of the locking cap, the spaced-apart ramped locking elements engaging said segments and locking the cap on the pour spout in fluid-tight engagement therewith when said locking cap is rotated, said ramped locking elements cooperating with the segments to force the locking cap more fully into the pour spout to seal the pour spout as the ramped locking elements slide along the ramps of the segments to a fully closed position at which the ramped locking elements have substantially reached the stops.

2. The cover for a suction container as claimed in claim 1, wherein the annular outer rim includes an edge portion disposed on the upper face of the cover overlying the annular flanges thereof, said annular rim including an outer descending wall adjacent the outermost annular flange.

3. The cover for a suction container as claimed in claim 2, wherein the outer descending wall of the rim terminates in an annular bead that structurally strengthens the cover.

4. The cover for a suction container as claimed in claim 3, wherein an annular space disposed between the descending wall of the rim and the annular flange adjacent thereto engages annular rim of a rigid canister comprising the suction container.

5. The cover for a suction container as claimed in claim 1, wherein the vacuum port comprises an opening within the cover that is disposed between the annular outer rim of the cover and the support cylinder, the vacuum port including a cylinder that extends both above the upper face and below the lower face of the cover.

6. The cover for a suction container as claimed in claim 5, wherein an annular skirt is disposed on the lower face of the cover below the vacuum port, the skirt being diametrically larger than and concentric with the vacuum port, one edge of the skirt truncating the support cylinder, and a bottom edge of the skirt extending substantially below a bottom edge of the vacuum port.

7. The cover for a suction container as claimed in claim 6, wherein the patient port comprises a tubular extension disposed between the annular rim and the support cylinder of the cover, extending substantially above the upper face of the cover and having a splash guard extending below the lower face of the cover, the splash guard facing the skirt of the vacuum port to deflect fluid drawn in through the patient port away from a lower end of the vacuum port.

8. The cover for a suction container as claimed in claim 1, wherein the pour spout comprises a tubular body portion having a lower end and an upper end, the lower end terminating at the lower face of the cover, and the upper end extending substantially above the upper face of the cover, said upper end truncating the support cylinder of the cover.

9. The cover for a suction container as claimed in claim 1, wherein the locking cap is rotatable into engagement with the pour spout in only one direction, said stops on the segments preventing the ramped locking elements from engaging the segments if the locking cap is rotated in an opposite direction.

10. The cover for a suction container as claimed in claim 1, wherein the segments have a detent formed therein to hold the ramped locking elements in a fully engaged position.

11. The cover for a suction container as claimed in claim 1, wherein the locking cap includes an upper engagement portion, said upper engagement portion including a closed cover overlying the tubular body of the locking cap as well as multiple gripping surfaces to facilitate rotation of the locking cap.

12. The cover of a suction container as claimed in claim 11, wherein the closed end of the tubular body of the locking cap includes spaced-apart support members extending from a center of the closed cover to an inner tubular wall, said support members each engaging the inner tubular wall at a point of intersection with a different one of the ramped locking elements of the locking cap disposed on said outer wall.

13. The cover for such a container as claimed in claim 1, wherein the locking cap includes a loop and a connecting link attached at one of the gripping portions of the locking cap to secure the locking cap to the cover by attaching the loop to the vacuum port.

* * * * *